(12) United States Patent
Lee et al.

(10) Patent No.: US 11,130,940 B2
(45) Date of Patent: Sep. 28, 2021

(54) DEVICE FOR IN VITRO CULTURE OF EMBRYOS AND FABRICATION METHOD THEREOF

(71) Applicant: KANGWON NATIONAL UNIVERSITY University-Industry Cooperation Foundation, Chuncheon-si (KR)

(72) Inventors: Seung Tae Lee, Chuncheon-si (KR); Jung Im Yun, Chuncheon-si (KR); Song Baek, Seoul (KR)

(73) Assignee: Kangwon National University University-Industry Cooperation Foundation, Chuncheon-si (KR)

( * ) Notice: Subject to any disclaimer, the term of this patent is extended or adjusted under 35 U.S.C. 154(b) by 198 days.

(21) Appl. No.: 16/014,163

(22) Filed: Jun. 21, 2018

(65) Prior Publication Data
US 2019/0062695 A1  Feb. 28, 2019

(30) Foreign Application Priority Data
Aug. 22, 2017 (KR) .......................... 10-2017-0105785

(51) Int. Cl.
| | | |
|---|---|---|
| *C12N 5/073* | (2010.01) | |
| *C12M 1/34* | (2006.01) | |
| *C12M 1/22* | (2006.01) | |
| *C12M 3/00* | (2006.01) | |
| *B01L 3/00* | (2006.01) | |

(Continued)

(52) U.S. Cl.
CPC .......... *C12N 5/0604* (2013.01); *B01L 3/5085* (2013.01); *C12M 21/06* (2013.01);
(Continued)

(58) Field of Classification Search
CPC .. C12N 5/0604; C12N 2533/30; C12N 5/061; C12N 2502/13; C12N 5/0606; C12M 23/20; C12M 23/12; C12M 21/06; C12M 23/10; C12M 41/32; C12M 33/04; B01L 3/5085; B01L 2200/12; B01L 2300/0829; B01L 2300/123; B01L 3/5027
See application file for complete search history.

(56) References Cited

U.S. PATENT DOCUMENTS 8,815,595 B2 * 8/2014 Iwanaga et al. ..... C12N 5/0062
435/402
9,260,684 B1 * 2/2016 Egeler et al. .......... C12M 23/12
(Continued)

FOREIGN PATENT DOCUMENTS

JP      2012157267 A  *  8/2012

OTHER PUBLICATIONS

Yasuhiko Koda, Plate member having fine pattern (JP2012157267A) Aug. 23, 2012, Google, (Translated Document), pp. 1-11. (Year: 2012).*

(Continued)

*Primary Examiner* — Gautam Prakash
(74) *Attorney, Agent, or Firm* — Rabin & Berdo, P.C.

(57) ABSTRACT

A device for in vitro culture of embryos includes: an array having at least one well formed therein; and a bottom surface formed in the well and made of polydimethylsiloxane (PDMS). The use of the culture vessel having the well bottom surface made of PDMS has the effect of further increasing the blastocyst formation rate of embryos compared to the use of conventional arrays made of plastic.

7 Claims, 4 Drawing Sheets

(51) Int. Cl.
| | |
|---|---|
| C12M 1/32 | (2006.01) |
| C12M 1/00 | (2006.01) |
| C12N 5/0735 | (2010.01) |
| C12M 1/26 | (2006.01) |
| C12N 5/076 | (2010.01) |

(52) U.S. Cl.
CPC ............ *C12M 23/10* (2013.01); *C12M 23/12* (2013.01); *C12M 23/20* (2013.01); *C12M 41/32* (2013.01); *B01L 3/5027* (2013.01); *B01L 2200/12* (2013.01); *B01L 2300/0829* (2013.01); *B01L 2300/123* (2013.01); *C12M 33/04* (2013.01); *C12N 5/061* (2013.01); *C12N 5/0606* (2013.01); *C12N 2502/13* (2013.01); *C12N 2533/30* (2013.01)

(56) References Cited

U.S. PATENT DOCUMENTS

| | | | |
|---|---|---|---|
| 2003/0030184 A1* | 2/2003 | Kim | C12M 41/46 264/325 |
| 2004/0228772 A1* | 11/2004 | Chen et al. | B01L 3/5085 422/400 |
| 2016/0244807 A1* | 8/2016 | Conoci et al. | B01L 7/52 |

OTHER PUBLICATIONS

Basak Balaban et al., "Blastocyst quality affects the success of blastocyst-stage embryo transfer", Fertility and Sterility, Aug. 2000, pp. 282-287, vol. 74, No. 2.

Cristina Lagalla et al., "A quantitative approach to blastocyst quality evaluation: morphometric analysis and related IVF outcomes", J. Assist Reprod Genet, 2015, pp. 705-712, vol. 32.

Seradar Coskun et al., "Day 5 versus day 3 embryo transfer: a controlled randomized trial", Human Reproduction, 2000, pp. 1947-1952, vol. 15, No. 9.

Gayle M. Jones et al., "Factors affecting the success of human blastocyst development and pregnancy following in vitro fertilization and embryo transfer", Fertility and Sterility, Dec. 1998, pp. 1022-1029, vol. 70, No. 6.

Jing-Jie Li et al., "Modifications of Human Growth Differentiation Factor 9 to Improve the Generation of Embryos From Low Competence Oocytes", Mol Endocrinol, Jan. 2015, pp. 40-52, vol. 1.

Seung A. Cheong et al., "Improvement in the blastocyst quality and efficiency of putative embryonic stem cell line derivation from porcine embryos produced in vitro using a novel culturing system", Molecular Medicine Reports, 2015, pp. 2140-2148, vol. 12.

Kristy Red-Horse et al., "Trophoblast differentiation during embryo implantation and formation of the maternal-fetal interface", The Journal of Clinical Investigation, 2004, pp. 744-754, vol. 114, No. 6.

Takayuki Koike et al., "In-vitro Culture with a Tilting Device in Chemically Defined Media During Meiotic Maturation and Early Development Improves the Quality of Blastocysts Derived from In-vitro Matured and Fertilized Porcine Oocytes", Journal of Reproduction and Development, 2010, pp. 552-557, vol. 56, No. 5.

\* cited by examiner

DEVICE FOR IN VITRO CULTURE OF EMBRYOS AND FABRICATION METHOD THEREOF

BACKGROUND OF THE INVENTION

Field of the Invention

The present invention relates to an in vitro culture device which is used to culture embryos in vitro, and more particularly to a device for in vitro culture of embryos, which can increase the blastocyst formation rate of embryos, and a method for fabricating the device.

Description of the Prior Art

Infertility in the low-fertility era has become a global problem, and the incidence of infertility is increasing rapidly due to decreased fertility of advanced age women, increased genital disease, increased stress and environmental pollution, and the like. Thus, the number of infertility treatment cases is increasing rapidly.

in order to overcome this infertility or sterility, various assisted reproductive technologies such as ovulation induction, intrauterine insemination (IUI), in vitro fertilization (IVF), embryo transfer (ET), intra-cytoplasmic sperm injection (ICSI) and the like have been used. However, these infertility treatments have problems in that they require high costs and the pregnancy success rate after one-cycle treatment is very low (about 15 to 25%). Thus, the treatment cycle is continuously repeated in order to increase the pregnancy success rate. However, despite these efforts, the pregnancy success rate is less than 50%, and female patients who receive infertility treatments are also required to sacrifice their physical, mental and cost aspects.

Among assisted reproductive technologies, a technology capable of efficiently producing intrauterinally implantable good-quality blastocysts in vitro is very important (Balaban et al., 2000; Lagalla et al., 2015). However, according to the technologies of producing blastocysts by in vitro culture of embryos, developed so far, the blastocyst formation rate is generally as low as about 25%. Thus, the development of new technology capable of overcoming this limitation has been urgently demanded (Coskun et al., 2000). The mass production of intrauterinally implantable good-quality blastocysts by single infertility treatment can greatly reduce the patient's pain during infertility treatment and can also greatly increase the pregnancy success rate by increasing the change of intrauterine embryo implantation.

Accordingly, various methods have been attempted to increase the efficiency of in vitro production of good-quality blastocysts (Jones et al., 1998; Coskun et al., 2000). However, most approaches have been focused on the development of in vitro culture media by the addition and removal of chemical factors capable of promoting blastocyst formation (Li et al., 2015; Cheong et al., 2015), and even this improvement in in vitro culture media showed an in vitro blastocyst production efficiency of not more than 40%. Thus, despite the optimization of culture media, limitations on the blastocyst formation rate were shown. To overcome these limitations, it is also important to improve in vitro culture environments based on physical factors rather than improving in vitro culture environments based on chemical factors.

PRIOR ART DOCUMENTS

Non-Patent Documents

1. Balaban B, Urman B, Sertac A, Aksoy S, Mercan R (2000): Blastocyst quality affects the success of blastocyst-stage embryo transfer. Fertil Steril 74:282-287.
2. Lagalla C, Barberi M, Orlando G, Sciajno R, Bonu M A, Borini A (2015): A quantitative approach to blastocyst quality evaluation: morphometric analysis and related IVF coutcomes. J Assist Reprod Genet 32:705-712.
3. Coskun S, Hollanders J, Ai-Hassan S, Al-Sufyan H, Al-Mayman H, Jaroudi K (2000): Day 5 versus day 3 embryo transfer: a controlled randomized trial. Hum Reprod 15:1947-1952.
4. Jones G M, Trounson A O, Lolatgis N, Wood C (1998): Factors affecting the success of human blastocyst development and pregnancy following in vitro fertilization and embryo transfer. Fertile Steril 70:1022-1029.
5. Li J J, Sugimura S, Mueller T D, White M A, Martin G A, Ritter L J, Liang X Y, Gilchrist R B, Mottershead D G (2015): Modifications of human growth differentiation factor 9 to improve the generation of embryos from low competence oocytes. Mol Endocrinol 29:40-52.
6. Cheong S A, Kim E, Kwak S S, Jeon Y, Hyun S H (2015): Improvement in the blastocyst quality and efficiency of putative embryonic stem cell line derivation form porcine embryos produced in vitro using novel culturing system. Mol Med Rep 12:2140-2148.
7. Red-Horse K, Zhou Y, Genbacev O, Prakobphol A, Roulk R, McMaster M, Fisher S J (2004): Trophoblast differentiation during embryo implantation and formation of the maternal-fetal interface. J Clin Invest 114:744-754.
8. KOIKE T, MATSUURA K, NARUSE K, FUNAHASHI H (2010): In-vitro culture with a tilting device in chemically defined media during meiotic maturation and early development improves the quality of blastocysts derived from in-vitro matured and fertilized porcine oocytes. J Reprod Dev 56:552-557.

SUMMARY OF THE INVENTION

When blastocysts from embryos are produced using conventional plastic-based embryo in vitro culture vessels which have been widely used, the rate of blastocyst formation is greatly influenced by the embryo manipulation environment, manipulation time, the skill of the operator, and the like. In addition, whether embryos are produced in vivo or produced in vitro also greatly influences the rate of blastocyst formation in plastic-based embryo in vitro culture vessels.

Therefore, it is an object of the present invention to develop an embryo in vitro culture vessel made of a new material, which can produce blastocysts from embryos with high efficiency while preventing the rate of blastocyst formation from being substantially influenced by external factors.

However, objects which are to be achieved by the present invention are not limited to the above-mentioned object, and other objects of the present invention will be clearly understood by those skilled in the art from the following description.

A first aspect of the present invention is directed to a device for in vitro culture of embryos, including: an array having at least one well formed therein; and a bottom surface formed in the well and made of polydimethylsiloxane (PDMS).

A second aspect of the present invention is directed to a device for in vitro culture of embryos, including: a solid body made of polydimethylsiloxane (PDMS); and at least one well formed in the solid body.

A third aspect of the present invention is directed to a method for fabricating a device for in vitro culture of embryos, the method including the steps of: preparing an array having at least one well formed therein; and forming a bottom surface made of polydimethylsiloxane (PDMS) in the well of the prepared array.

A fourth aspect of the present invention is directed to a method for fabricating a device for in vitro culture of embryos, the method including the steps of: mixing liquid polydimethylsiloxane with a curing agent, thereby preparing a mixture solution; removing bubbles from the prepared mixture solution; and pouring the mixture solution, from which the bubbles have been removed, into a mold having at least one well-forming structure, and curing the mixture solution.

A fifth aspect of the present invention is a method for in vitro culture of embryos, including the steps of: injecting embryos into the well of the device for in vitro culture; and culturing the embryos.

The above-described technical solutions are only illustrative and are not intended to limit the scope of the present invention. In addition to the above-described exemplary embodiments, additional embodiments and examples as described in the following detailed description may be contemplated.

DETAILED DESCRIPTION OF THE INVENTION

Hereinafter, embodiments of the present invention will be described in detail with reference to the accompanying drawings so that they can be readily implemented by those skilled in the art. However, the present invention may be embodied in a variety of different forms and should not be construed as limited to the embodiments set forth herein. In the drawings, parts unrelated to the description are omitted to clearly explain the present invention.

Throughout the specification, when any part is referred to as "including" any component, it does not exclude other components, but may further include other components, unless otherwise specified.

Through the specification, words of degree, such as "about", "substantially", and the like are used herein in the sense of "at, or nearly at, when given the manufacturing and material tolerances inherent in the stated circumstances" and are used to prevent the unscrupulous infringer from unfairly taking advantage of the invention disclosure where exact or absolute figures are stated as an aid to understanding the invention. As used herein, the term "step of doing ~" or "step of ~" does not mean "step for ~".

Throughout the specification, the term "combination thereof" included in the Markush type expression refers to a mixture or combination of one or more selected from the group consisting of constituent elements described in the Markush type expression, and means including one or more selected from the group consisting of the aforementioned constituent elements.

Throughout the specification, the description "A and/or B" means "A, B, or A and B".

Hereinafter, a device for in vitro culture of embryos according to the present invention, a method for fabricating the same, and a method for in vitro culture of embryos using the same will be described in detail with reference to exemplary embodiments, examples and the accompanying drawings. However, the scope of the present invention is not limited to these exemplary embodiments, examples and drawings.

Figure 1:
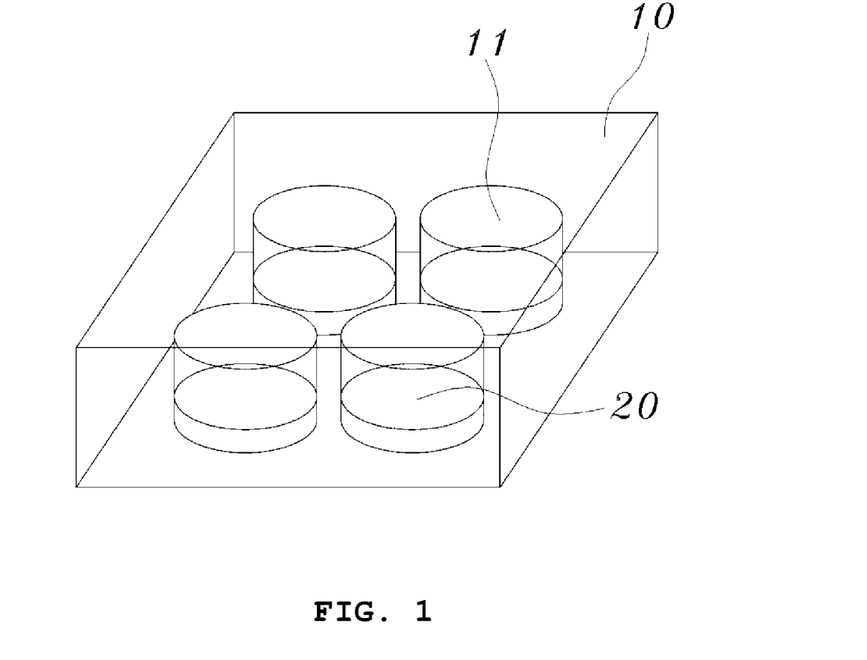
FIG. 1 is a perspective view showing the configuration of a device for in vitro culture of embryos according to one embodiment of the present invention.

FIG. 1 is a perspective view showing the configuration of a device for in vitro culture of embryos according to one embodiment of the present invention.

As shown therein, a first aspect of the present invention is directed to a device for in vitro culture of embryos, including: an array 10; and a bottom surface 20.

The array 10 has at least one well 11 formed therein. The well 11 may be a groove formed in a solid body. In addition, the well 11 may be formed in plural numbers in the solid body in an arrayed manner. This array is not particularly limited, and the present invention may include various arrays known in the art. Since the present invention may also use arrays which have been frequently used in the art, the device may be fabricated in a simple and easy manner. In addition, if necessary, the user may also directly fabricate the device using a conventional array and use the fabricated device.

The bottom surface 20 is formed in the well 11 and made of polydimethylsiloxane (PDMS). Namely, a bottom surface made of PDMS is formed on the bottom of the well 11 of the array 10. This bottom surface 20 may be liquid or solid PDMS. In particular, the bottom surface 20 is preferably made of solid PDMS, and in this case, embryos are more effectively cultured thereon. A method for forming the bottom surface 20 made of PDMS is not particularly limited. The bottom surface 20 may have a flat structure and may also have a two- or three-dimensional shape. Furthermore, according to the present invention, not only the bottom surface 20 of the well 11, but also the whole or a portion of the side may be coated with PDMS.

The present invention is characterized in that the bottom of the well 11 of the array 10 is made of PDMS, in which the PDMS mimics an in vivo environment in which embryos can grow.

Embryos that are used in the specification are cells having the potential to form single complete individuals, unlike common animal cells, and culture conditions (media, factors, culture environments and the like) and developmental stages thereof are also distinguished from those of common animal cells. Namely, even culture environments suitable for common animal cells including stem cells may be unsuitable for the culture and/or development of embryos, and even culture environments suitable for the culture and/or development of embryos may be unsuitable for culture of common animal cells. For example, the embryos may be embryos of mice, rats, humans, pigs, cattle, dogs, monkeys, horses, sheep or zebrafishes, but are not limited thereto.

In fact, the present inventors have found that, as described in Examples below, when an array 10 including a well 11 having a bottom surface 20 made of PDMS is used, the efficiency of blastocyst production from embryos greatly increases compared to when a conventional array made of only a plastic material is used, thereby completing the present invention.

The results of experiments performed by the present inventors indicated that even when an array including each well having a bottom surface made of PDMS was used, the developmental rate of embryos to the 2-cell stage was lower compared to when an array made of only a plastic material, and there was no great significance in the rate of development to the 4-cell stage (see Example 1 of the present invention). Thus, in the prior art, it would not have been easy to think that even if a bottom surface made of PDMS is formed in a well, the rate of blastocyst formation will greatly increase.

However, the present inventors have also investigated the efficiency of blastocyst production from embryos, and have newly found that when a culture vessel including a well 11 having a bottom surface 20 made of PDMS as disclosed in the present invention is used, the blastocyst formation rate of embryos greatly increases.

The present invention exhibits the effect of further increasing the blastocyst formation rate of embryos compared to a conventional art by including a bottom surface 20 made of PDMS while using a conventional array.

Thus, the in vitro culture device according to the present invention is more preferably a device for culturing embryos in vitro to the blastocyst stage.

Figure 2:
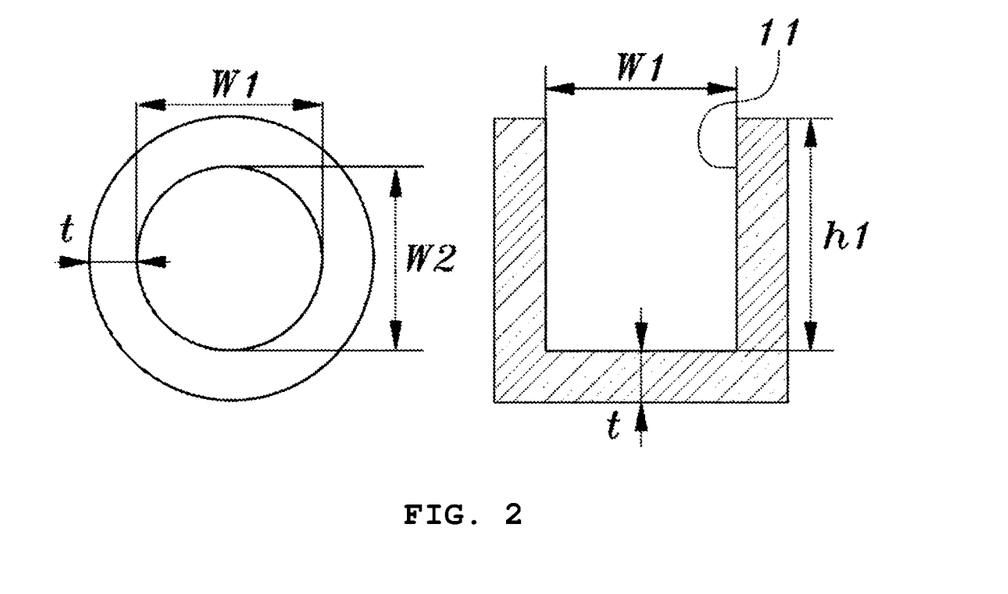
FIG. 2 is a cross-sectional view showing an example of the well structure of a device for in vitro culture of embryos according to the present invention.

FIG. 2 is a cross-sectional view showing an example of the structure of the well 11 of the in vitro culture device 1 according to the present invention.

In one embodiment of the present invention as shown in FIG. 2, the side cross-section of the well 11 may be vertical. Namely, the top of the well 11 has a size or area equal or similar to that of the bottom. In other words, the diameter of the top of the well is equal or similar to the diameter of the bottom, and thus embryos to be cultured and medium for culturing the same may be easily injected into the well 11.

For example, the width ($w_1$, $w_2$) of the well is not particularly limited, but is preferably in the range of 1 mm to 50 mm, 2 mm to 40 mm, 3 mm to 30 mm, 4 mm to 25 mm, 5 mm to 20 mm, 6 mm to 15 mm, 7 mm to 13 mm, 8 mm to 12 mm, or 9 mm to 11 mm. In addition, the height ($h_1$) of the well 11 is not particularly limited, but is preferably in the range of 1 mm to 50 mm, 2 mm to 40 mm, 3 mm to 30 mm, 4 mm to 25 mm, 5 mm to 20 mm, 6 mm to 15 mm, 7 mm to 13 mm, 8 mm to 12 mm, or 9 mm to 11 mm. Namely, the well 11 may have a width ($w_1$, $w_2$) and height ($h_1$) in the same or similar range, so that the effect of culturing embryos therein can further be increased.

In addition, the thickness (t) of the well 11 may be about 1 mm to 1 cm, about 3 mm to 1 cm, about 6 mm to 1 cm, about 1 mm to 6 mm, or about 3 mm to 6 mm. Where an embryo-receiving part is formed on the wall surface and/or the bottom, the thickness of the well may become thicker, but is not limited thereto.

In another embodiment of the present invention, the cross-sectional shape of the well 11 may be wider at the top and narrower at the bottom. Namely, the top of the well 11 has a larger size or area than that of the bottom. In other words, the diameter of the top of the well 11 is greater than the diameter of the bottom, and thus the well 11 may have a larger opening at the inlet, through which embryos to be cultured and medium for culturing the same may be easily injected into the well 11.

Figure 3:
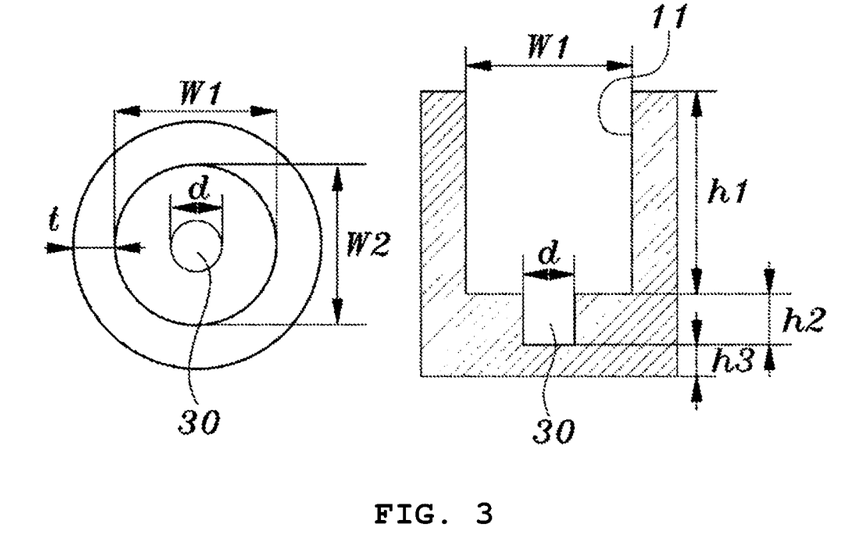
FIG. 3 is a cross-sectional view showing an example of a structure in which a groove is formed in the well of a device for in vitro culture of embryos according to the present invention.

FIG. 3 is a cross-sectional view showing an example of a structure in which a groove 30 is formed in the well 11 of the in vitro culture device according to the present invention.

In another embodiment of the present invention as shown in FIG. 3, the well 11 may include a groove 30 formed in the bottom surface 20.

The groove 30 may have a cylindrical, spherical or oval shape, and the cross-section thereof may be rectangular in shape as shown in FIG. 3, but is not particularly limited thereto. The groove 30 may be formed in the bottom surface 20 and/or side surface of the well 11, and may be formed to be recessed from the inner surface of the well 11. The diameter of the groove 30 may be about 2 mm to 5 mm, about 3 mm to 4 mm or about 3.5 mm, and the depth may be about 2 mm to 5 mm, about 3 mm to 4 mm, or about 3.5 mm, but are not limited thereto.

This groove 30 may have a size or shape capable of receiving embryos and/or medium, and serves as an embryo-receiving part. For example, the groove 30 may receive one embryo, but is not limited and may also receive two or more embryos.

As can be seen in the Examples below, the present inventors compared the efficiency of blastocyst formation between a well 11 having a flat bottom and a well 11 having a cylindrical grove 30, and as a result, found that the efficiency of blastocyst formation further increased when the well 11 having the groove 30 formed in the bottom surface was used.

In the present invention, a method for forming the bottom surface 20 is not particularly limited. For example, the bottom surface 20 is preferably formed by curing polydimethylsiloxane (PDMS). More preferably, the bottom surface 20 is formed by removing bubbles from liquid polydimethylsiloxane (PDMS) injected into the well 11 and then curing the PDMS.

This method for forming the bottom surface 20 made of PDMS will be described in more detail below.

Figure 4:
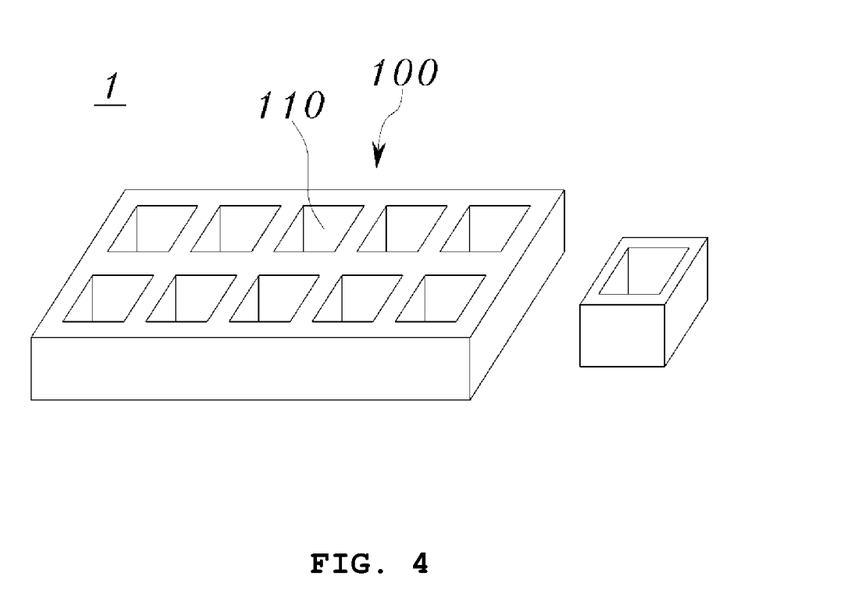
FIG. 4 is a perspective view showing the configuration of a device for in vitro culture of embryos according to another embodiment of the present invention.

FIG. 4 is a perspective view showing the configuration of a device for in vitro culture of embryos according to another embodiment of the present invention.

A second aspect of the present invention is directed to a device for in vitro culture of embryos, including: a solid body 100 made of polydimethylsiloxane (PDMS); and at least one well formed in the solid body 100.

The solid body 100 may be in the form of a culture dish for in vitro culture for embryos, a culture plate, a culture flask, or other forms for culture, and is composed essentially of polydimethylsiloxane (PDMS), a kind of silicone.

The well 110 may be formed by any method which is used for molding of PDMS in the art. For example, it may be formed by a method using a mold or by a lithography method, but is not limited thereto.

In the well 100 formed in the solid body 100, embryos may be cultured in the presence of medium. The solid body 100 made of PDMS may mimic an in vivo environment in which embryos grow.

This in vitro culture device may be particularly a device optimized for in vitro culture of embryos. For example, the in vitro culture device of the present invention, which includes the solid body 100 made of PDMS, has a number of pores, and thus mimics an in vivo environment in which embryos grow. Thus, it can further increase the culture and/or developmental rate of embryos compared to in vitro culture devices made of other materials.

According to the present invention, the well 100 may be formed in plural numbers in the solid body 100 in an arrayed manner, but is not limited thereto. For example, the wells 100 may be arranged in various array structures, including one or more lanes, a lattice configuration or a clustered configuration.

Figure 5:
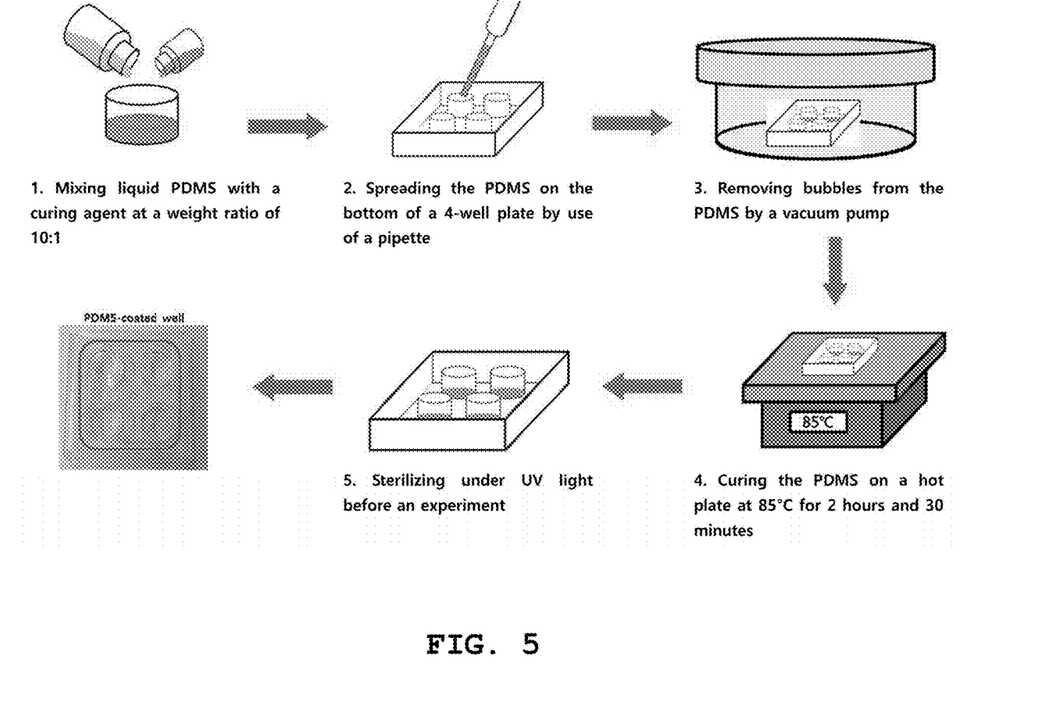
FIG. 5 is a flow chart illustrating an example of a method for fabricating an in vitro culture device having a bottom surface made of PDMS according to the present invention.

FIG. 5 is a flow chart illustrating an example of a method for fabricating an in vitro culture device having a bottom surface made of PDMS according to the present invention.

A third aspect of the present invention as shown in FIG. 5 is directed to a method for fabricating a device for in vitro culture of embryos, the method including the steps of: (S10) preparing an array having at least one well formed therein; and (S20) forming a bottom surface made of polydimethylsiloxane (PDMS) in the well of the prepared array.

Step (S10) of arraying the array is a step of preparing an array having at least one well formed therein. Examples of the array include all arrays known in the art.

Step (S20) of forming the bottom surface is a step of forming a bottom surface made of polydimethylsiloxane (PDMS) in the well of the prepared array.

For example, step (S20) of forming the bottom surface may include the steps of: (S21) injecting liquid polydimethylsiloxane (PDMS) into the well of the prepared array; (S22) removing bubbles from the injected polydimethylsiloxane; and (S23) curing the polydimethylsiloxane from which the bubbles have been removed.

In addition, removing the bubbles may be achieved by placing in a vacuum chamber the array having the polydimethylsiloxane injected therein and removing bubbles from the polydimethylsiloxane.

Figure 6:
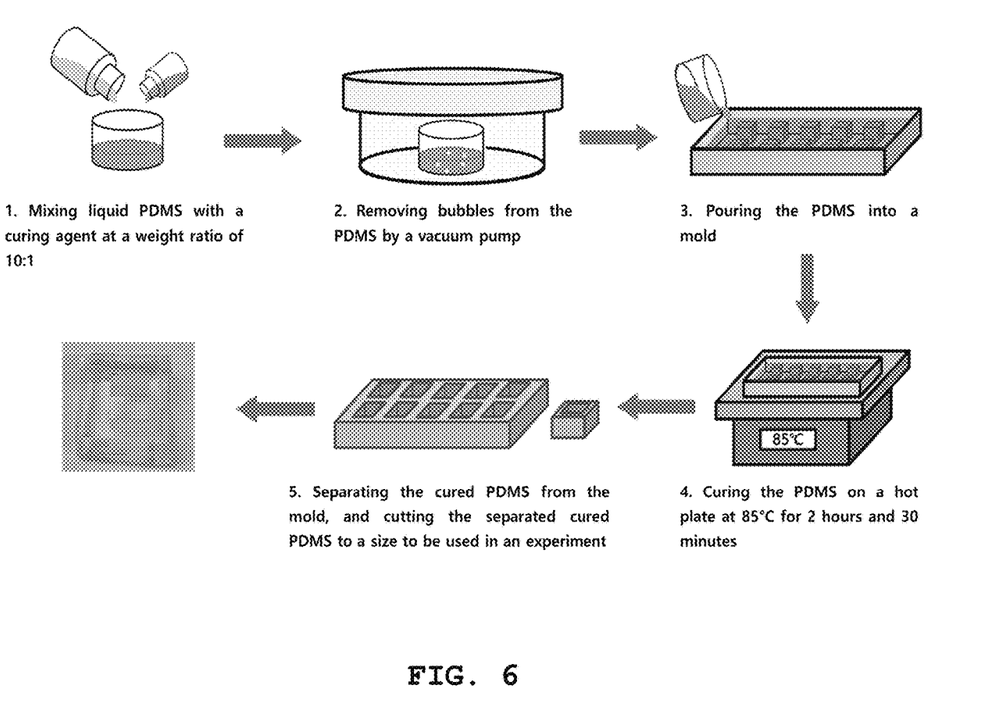
FIG. 6 is a flow chart illustrating an example of a method for fabricating an in vitro culture device having a body made of PDMS according to the present invention.

FIG. 6 is a flow chart illustrating an example of a method for fabricating an in vitro culture device having a bottom surface made of PDMS according to the present invention.

A fourth aspect of the present invention as shown in FIG. 6 is directed to a method for fabricating a device for in vitro culture of embryos, the method including the steps of: (S110) mixing liquid polydimethylsiloxane with a curing agent, thereby preparing a mixture solution; (S120) removing bubbles from the prepared mixture solution; and (S130) pouring the mixture solution, from which the bubbles have been removed, into a mold having at least one well-forming structure, and curing the poured mixture solution.

Specifically, the method for fabricating the in vitro culture device according to the present invention may include: mixing liquid polydimethylsiloxane with a curing agent, thereby preparing a mixture solution; removing bubbles from the mixture solution; and curing the mixture solution, thereby forming a solid body having a well.

The polydimethylsiloxane (PDMS), a flowable material, has the property of being cured by the curing agent at room temperature or high temperature with the passage of time, thereby forming a solid. It may be mixed with the curing agent at a predetermined ratio to form a PDMS mixture which may then be fed and cured in a mold, but is not limited thereto. For example, the PDMS mixture may be prepared into solid bodies having various shapes depending on the shape of the mold, but is not limited thereto.

For example, a groove as an embryo-receiving part may further be formed in the bottom or wall surface of the well, but the scope of the present invention is not limited thereto.

According to one embodiment of the present invention, the curing agent is not particularly limited, and may be suitably selected by those skilled in the art from among curing agents which are used for curing of silicones such as PDMS in the art.

According to one embodiment of the present invention, the liquid polydimethylsiloxane and the curing agent may be mixed with each other at a weight of about 50:1 to 2:1, but the scope of the present invention is not limited thereto. For example, the liquid polydimethylsiloxane and the curing agent may be mixed with each other at a weight ratio of about 30:1 to 2:1, about 20:1 to 2:1, about 10:1 to 2:1, about 5:1 to 2:1, about 50:1 to 5:1, about 50:1 to 10:1, about 50:1 to 20:1, about 30:1 to 5:1, or about 10:1, but the scope of the present invention is not limited thereto.

For example, the PDMS may be cured at room temperature or high temperature. Where it is cured at high temperature, it may be cured using heating devices, including an oven, a warm plate and a hot plate, but is not limited thereto. As the curing temperature increases, the curing time may be shortened.

According to one embodiment of the present invention, removing bubbles from the mixture solution may be performed using a vacuum pump, but is not limited thereto. In addition, for removal of bubbles, any method may be used without limitation, as long as it is a method which is used to remove bubbles from liquid solutions in the art. For example, the removal of bubbles may be achieved by placing the prepared mixture solution in a vacuum chamber and removing bubbles from the polydimethylsiloxane in the vacuum chamber.

According to one embodiment of the present invention, the curing may be performed at a temperature of about 60° C. to 100° C. for about 1 to 5 hours, but is not limited thereto. For example, the curing may be performed at a temperature of about 60° C. to 90° C., about 60° C. to 80° C., about 60° C. to 70° C., about 70° C. to 100° C., about 80° C. to 100° C., about 90° C. to 100° C., about 80° C. to 90° C., or about 85° C., but is not limited thereto. For example, the curing may be performed for about 1 to 4 hours, about 1 to 3 hours, about 1 to 2 hours, about 2 to 5 hours, about 3 to 5 hours, about 4 to 5 hours, about 2 to 3 hours, or about 2 hours and 30 minutes, but is not limited thereto.

According to one embodiment of the present invention, the method for fabricating the in vitro culture device may further include a step of sterilizing the solid body, but the scope of the present invention is not limited thereto. The sterilizing step may be performed for the purpose of preventing embryos from being contaminated with external bacteria, bacteria or contaminants during in vitro culture of embryos, but is not limited thereto. The sterilizing step may be performed using any sterilization process which is used in the art. For example, it may be performed by UV radiation, irradiation, heat treatment, chemical treatment, autoclaving or the like, but is not limited thereto.

According to one embodiment of the present invention, the mold may have two or more well-forming structures, and the method of the present invention may further include a step of separating the cured material from the mold, and cutting the separated cured material into portions, each including one well. For example, the solid body 100 having a plurality of wells 100 formed therein may be cut or separated into portions, each including one well 110, and may be used for in vitro culture, but the scope of the present invention is not limited thereto.

A fifth aspect of the present invention is directed to a method for in vitro culture of embryos, including the steps of: injecting embryos into the well of the in vitro culture device; and culturing the embryos.

Specifically, the present invention may provide a method for in vitro culture of embryos, which includes culturing embryos to the blastocyst stage in the presence of medium in a cell culture device made of polydimethylsiloxane, but the scope of the present invention is not limited thereto.

The embryos cultured to the blastocyst stage may be transferred into the animal uterus or may be used for extraction of stem cells, but the scope of the present invention is not limited thereto. For example, the animal may be the same as or different from an animal from which the embryos originated.

According to one embodiment of the present invention, the method for in vitro culture of embryos may include culturing 1-cell-stage embryos to the blastocyst stage, but is not limited thereto and may be used in any stage among the developmental stages of embryos.

According to one embodiment of the present invention, after the embryos reach the 4-cell stage, they may be cultured to the blastocyst stage in fresh medium containing BSA, but the scope of the present invention is not limited thereto.

According to one embodiment of the present invention, the medium may include M16 medium, but is not limited thereto and any selected medium which is used for culture of embryos in the art.

According to one embodiment of the present invention, the method for culture of embryos may show an increased rate of blastocyst formation compared to methods that do not use the cell culture device made of polydimethylsiloxane, but the scope of the present invention is not limited thereto.

Hereinafter, the present invention will be described in further detail with reference to examples. It is to be understood, however, that these examples are for illustrative purposes only and are not intended to limit the scope of the present invention.

Examples

1. Materials and Method
1.1. Animals

In this Example, 9-week-old female ICR mice and 9-week-old male ICR mice were used, which were all purchased from Dae Han Bio Link Co., Ltd. (Korea). All animal experiments performed were approved by the Animal Experiments Ethical Committee of Kangwon National University (No: KW-170117-1).

1.2. Fabrication of PDMS-Coated Plastic Culture Dish

A schematic representation for fabrication of a PDMS-coated plastic culture dish is shown in FIG. 2. Specifically, PDMS (polydimethylsiloxane; Dowdoring, Seoul, Korea), a kind of silicone, was mixed with a curing agent at a ratio of 10:1 (wt/wt). The PDMS mixture solution was applied to the entire bottom of a 4-well dish by use of a pipette. Then, the 4-well dish having the PDMS solution applied thereto was placed in a container connected to a vacuum pump, and a vacuum was applied thereto, thereby removing bubbles from the PDMS solution. The PDMS solution, from which bubbles have been removed, was cured on a hot plate at 85° C. for 2 hours. The 4-well dish coated with the completely cured PDMS was sterilized by 15 minutes of UV treatment, and then used for in vitro culture of embryos.

1.3. Fabrication of Culture Dish Made of PDMS

A schematic representation for fabrication of a culture dish made of PDMS is shown in FIG. 3. Specifically, PDMS was mixed with a curing agent at a ratio of 10:1 (wt/wt). The mixture solution was placed in a container connected to a vacuum pump, and a vacuum was applied thereto, thereby removing bubbles from the PDMS solution. The mixture solution, from which bubbles have been removed, was filled into each of culture dish molds having the dimensions shown in FIG. 4a (a culture dish having a flat bottom) and FIG. 4b (a culture dish having a cylinder-shaped hole), and was then cured on a hot plate at 85° C. for 2 hours and 30 minutes. The completely cured PDMS was separated from the molds, sterilized with UV light, and then used for in vitro culture of embryos.

1.3. Design of Experiments

In order to examine a difference in the efficiency of in vitro culture of embryos between culture dish materials or coating materials and to determine a culture dish material exhibiting the optimal efficiency, each of in vivo fertilized embryos and in vitro fertilized embryos was cultured in vitro in each of a plastic 4-well culture dish (plastic), a culture dish made of PDMS without plastic (PDMS) and a PDMS-coated plastic 4-well culture dish (PDMS+ plastic). After 5 days of in vitro culture, the efficiency of blastocyst formation in each of the experimental groups was evaluated. In addition, in order to determine the bottom structure of the PDMS culture dish optimized for improvement in the efficiency of in vitro culture of embryos, each of in vivo fertilized embryos and in vitro fertilized embryos was cultured in vitro in each of a PDMS culture dish having a flat bottom structure (flat bottom) and a PDMS culture dish having a cylinder-shaped hole (cylinder-shaped hole) for 5 days, and the efficiency of blastocyst formation in each of the experimental groups was evaluated.

1.5. Production of In Vivo Fertilized Embryos

In order to induce superovulation in a female mouse, 5 IU pregnant mare serum gonadotropin (PMSG; Sigma-Aldrich) was injected intraperitoneally into a 9-week-old female ICR mouse, and after 48 hours, 5 IU human chorionic gonadotropin (hCG; LG Life Sciences) was injected intraperitoneally into the same female mouse. Subsequently, the super-ovulation-induced female mouse was mated with a 9-week-old male ICR mouse, and the success of mating was confirmed by the presence of a genital plug in the female mouse. At 18 hours after hCG was injected intraperitoneally into the female mouse, the female mouse was sacrificed by cervical dislocation, and the oviduct was dissected and added to 0.5% (wt/v) BSA (bovine serum albumin)-containing PBS (phosphate buffered saline) pre-warmed to 37° C. The embryos obtained from the fallopian tube by use of a capillary pipette were transferred to M2 medium containing 0.2% (wt/v) hyaluronidase and was incubated for 1 minute, thereby completely removing cumulus cells from the embryos. Next, embryos having both a pronucleus and a second polar body were selected under a stereomicroscope and used in in vitro culture.

1.5. Production of In Vitro Fertilized Embryos

Mature oocytes were prepared as follows: 5 IU pregnant mare serum gonadotropin (PMSG; Sigma-Aldrich) was injected intraperitoneally into a 9-week-old female ICR mouse, and after 48 hours, 5 IU human chorionic gonadotropin (hCG; LG Life Sciences) was injected intraperitoneally into the same female mouse. At 16 hours after hCG was injected intraperitoneally into the female mouse, the female mouse was sacrificed by cervical dislocation, and the oviduct was dissected and added to 0.5% (wt/v) BSA-containing PBS pre-warmed to 37° C. The dissected oviduct was transferred to a Petri dish containing 2 ml of M2 medium (Sigma-Aldrich) on a hot plate at 37° C., and the fallopian tube was cut using forceps, thereby retrieving cumulus-oocyte cell complexes. Mature sperms were prepared as follows: a 9-week-old male ICR mouse was sacrificed by cervical dislocation, and then the epididymis of the male mouse was dissected and added to PBS containing 0.5% (wt/v) bovine serum albumin (BSA). The epididymis was defatted using forceps on a hot plate at 37° C., and then transferred to fresh PBS. The defatted epididymis was transferred again to a Petri dish containing 2 ml of M16 medium supplemented with 2.7 mM calcium, and then the epididymal tail was cut and the epididymis was incubated at 37° C. in a 5% $CO_2$ atmosphere for 20 minutes, thereby retrieving sperms from the epididymis tail. The mature sperms retrieved from the epididymal tail were further cultured in M16 medium containing 2.7 mM calcium at 37° C. in a 5% $CO_2$ atmosphere for 90 minutes, thereby inducing capacitation of the mature sperms. The total number of capacitated mature sperms was measured using a blood cell counting chamber. In vitro fertilization of the mature oocytes with the capacitated mature sperms was performed as follows. $5\times10^5$ capacitated sperms were cultured in M16 medium containing cumulus-oocyte cell complexes at 37° C. in a 5% $CO_2$ atmosphere for 6 hours. Next, embryos having both a pronucleus and a second polar body were selected under a stereomicroscope and used in in vitro culture.

1.7. In Vitro Culture

The in vitro fertilized embryos retrieved as described above were cultured in M16 medium in the culture dish (prepared in this Example) at 37° C. in a 5% $CO_2$ atmosphere. After 48 hours of culture, the embryos developed to the 4-cell stage were transferred to M16 medium further containing 3 mg/ml BSA. Then, the 4-cell embryos were further cultured for 72 hours without replacing medium.

1.8. Statistical Analysis

All the experimental results obtained in this Example were statistically analyzed using the general linear model (PROC-GLM) in the statistical analysis system (SAS) program, and significance tests for each experiment were performed using the Analysis of Variance (ANOVA) Procedure included in the SAS package. Next, a significant difference between treatment groups was measured using the Least-Square or DUNCAN method. In addition, P value <5% was considered significant between the treatment groups.

2. Results 2.1. Results of Culture of In Vivo Fertilized Embryos

After the superovulation-induced female ICR mouse was mated with the male ICR mouse according to the above-described method, the embryos produced in vivo were retrieved. The retrieved in vivo fertilized embryos were cultured in each of a culture dish made of plastic which has been widely used as a culture dish material in the art (control, plastic), a culture dish made of PDMS (PDMS), and a culture dish fabricated by coating PDMS on the bottom of a culture dish made of plastic (plastic+ PDMS) at 37° C. in a 5% $CO_2$ atmosphere for 5 days.

As shown in Table 1 below, for the rate of development to the 2-cell stage, the in vivo fertilized embryos cultured in each of [PDMS] and [plastic] showed a higher developmental rate than those cultured in [plastic+ PDMS]. In addition, for the rate of development to the 4-cell stage, the in vivo fertilized embryos cultured in each of [PDMS] and [plastic+ PDMS] showed a higher developmental rate than those cultured in [plastic].

However, when the rate of blastocyst formation was compared, changed results were obtained. Specifically, the in vivo fertilized embryos cultured in [PDMS] showed the significantly highest rate of blastocyst formation. In addition, the in vivo fertilized embryos cultured in [plastic] did not form blastocysts, and the in vivo fertilized embryos cultured in [plastic PDMS] showed a significantly higher rate of blastocyst formation compared to the in vivo fertilized embryos cultured in [plastic].

TABLE 1

Effects of different materials of culture plates used for in-vitro culture on preimplantation development of 1-cell embryos retrieved from naturally mated female ICR mouse

| Materials | No. of embryos[b] cultured | No. (%)[c] of embryos developed to | | |
|---|---|---|---|---|
| | | 2-cell [42][d] | 4-cell [66][d] | Blastocyst [138][d] |
| Plastic | 139 | 133 (95.7)[e] | 90 (67.7)[e] | 0 (0)[e] |
| PDMS | 138 | 136 (98.6)[e] | 122 (88.4)[f] | 78 (56.5)[f] |
| Plastic + PDMS[a] | 130 | 105 (80.8)[f] | 95 (73.1)[e] | 54 (41.5)[g] |

Model effects of treatments in each parameter, as indicated by p values, were <0.0001, 0.0056 and <0.0001 in the development to the 2-cell, 4-cell and blastocyst stages, respectively.
[a]PDMS-coated plastic culture dish.
[b]1-cell embryos were retrieved by oviduct flushing 18 hours post-hCG injection.
[c]Percentage relative to the number of embryos cultured.
[d]Numbers in parentheses indicate hours post-hCG injection.
Embryos were cultured in BSA-free M16 medium from the onset of culture and BSA (3 mg/ml) was added to M16 medium from 66 hours post-hCG injection.
[e-g]Different subscripts within the same column are significantly different (p < 0.05).

These results indicate that when a culture dish made of a silicone material such as PDMS is used for in vitro culture of in vivo fertilized embryos, the efficiency of blastocyst production can be greatly increased compared to when a culture dish made of plastic which has been used in the prior art.

Next, in order to confirm the bottom structure of a PDMS-based culture dish efficient for in vitro culture of embryos, in vivo fertilized embryos were cultured in each of a PDMS-based culture dish having a flat bottom structure (flat bottom) and a PDMS-based culture dish having a cylinder-shaped hole (cylinder-shaped hole) at 37° C. in a 5% $CO_2$ atmosphere for 5 days.

As shown in Table 2 below, the in vivo fertilized embryos cultured in the PDMS-based culture dishes having each of the [flat bottom] and [cylinder-shaped hole] structures showed no significant difference in the rate of development to the 2-cell stage, but the rates of development of the in vivo fertilized embryos to the 4-cell and blastocyst stages were significantly higher in the PDMS-based culture dish having the cylinder-shaped hole structure than in the PDMS-based culture dish having the flat bottom structure.

TABLE 2

Effects of bottom structure of PDMS-based culture plates used for in-vitro culture on preimplantation development of 1-cell embryos retrieved from naturally mated female ICR mouse

| Bottom structure of PDMS-based culture plates | No. of embryos[b] cultured | No. (%)[c] of embryos developed to | | |
|---|---|---|---|---|
| | | 2-cell [42][d] | 4-cell [66][d] | Blastocyst [138][d] |
| Flat | 131 | 111 (84.7) | 93 (71.0)[e] | 73 (55.7)[e] |
| Cylinder-shaped hole[a] | 127 | 112 (88.2) | 104 (81.9)[f] | 88 (69.3)[f] |

Model effects of treatments in each parameter, as indicated by p values, were 0.7151, 0.0074 and 0.0057 in the development to the 2-cell, 4-cell and blastocyst stages, respectively.
[a]Bottom has a cylinder-shaped hole with 3.5 mm diameter and 4 mm height and 1-cell embryos were cultured in this chamber.
[b]One-cell embryos were retrieved by oviduct flushing 18 hours post-hCG injection.
[c]Percentage relative to the number of embryos cultured.
[d]Numbers in parentheses indicate hours post-hCG injection.
Embryos were cultured in BSA-free M16 medium from the onset of culture and BSA (3 mg/ml) was added to M16 medium from 66 hours post-hCG injection.
[e,f]Different subscripts within the same column indicate significant differences, $p < 0.05$.

These results demonstrate that the use of the PDMS-based culture dish having the cylinder-shaped hole structure can greatly increase the efficiency of production of blastocysts from in vivo fertilized embryos. Thus, it is expected that the PDMS-based culture dish having the cylinder-shaped hole structure can be of great help in the mass production of blastocysts from in vivo fertilized embryos.

2.2. Results of Culture of In Vitro Fertilized Embryos

The mature oocytes retrieved from the superovulation-induced female ICR mouse according to the above-described method were fertilized in vitro with the mature sperms retrieved from the epididymis of the male ICR mouse, thereby producing in vitro fertilized embryos. Next, the produced in vitro fertilized embryos were cultured in each of a culture dish made of plastic which has been widely used as a culture dish material in the art (control, plastic), a culture dish made of PDMS (PDMS), and a culture dish fabricated by coating PDMS on the bottom of a culture dish made of plastic (plastic+ PDMS) at 37° C. in a 5% $CO_2$ atmosphere for 5 days.

As shown in Table 3 below, for the rate of development to the 2-cell stage, the in vitro fertilized embryos cultured in each of [plastic] and [plastic+ PDMS] showed a significantly higher rate of development to the 2-cell stage than the in vitro fertilized embryos cultured in [PDMS]. In addition, for the rate of development to the 4-cell stage, the in vitro fertilized embryos cultured in [plastic+ PDMS] showed a higher developmental rate than the in vitro fertilized embryos cultured in [plastic] and [PDMS].

However, the rate of blastocyst formation was significantly higher in the in vitro fertilized embryos cultured in [PDMS] than in the in vitro fertilized embryos cultured in [plastic+ PDMS]. In addition, the in vitro fertilized embryos cultured in [plastic] did not form blastocysts.

TABLE 3

Effects of different materials of culture plates used for in-vitro culture on preimplantation development of 1-cell ICR mouse embryos generated through in-vitro fertilization

| Materials | No. of embryos[b] cultured | No. (%)[c] of embryos developed to | | |
|---|---|---|---|---|
| | | 2-cell [48][d] | 4-cell [72][d] | Blastocyst [144][d] |
| Plastic | 63 | 60 (95.2)[e,f] | 60 (95.2)[e] | 0 (0)[e] |
| PDMS | 65 | 57 (87.7)[e] | 54 (83.1)[e,f] | 39 (60.0)[f] |
| Plastic + PDMS[a] | 61 | 60 (98.4)[f] | 45 (73.8)[f] | 27 (44.3)[g] |

Model effects of treatments in each parameter, as indicated by p values, were <0.0001, 0.0056 and <0.0001 in the development to the 2-cell, 4-cell and blastocyst stages, respectively.
[a]PDMS-coated plastic culture dish.
[b]One-cell embryos with pronucleus and second polar body were collected at 6 hours after incubating mature oocytes retrieved by oviduct flushing 16 hours post-hCG injection with spermatozoa.
[c]Percentage relative to the number of embryos cultured.
[d]Numbers in parentheses indicate hours post-hCG injection.
Embryos were cultured in BSA-free M16 medium from the onset of culture and BSA (3 mg/ml) was added to M16 medium from 72 hours post-hCG injection.
[e-g]Different subscripts within the same column indicate are significantly different ($p < 0.05$).

These results indicate that when a culture dish made of a silicone material such as PDMS is used for in vitro culture of in vitro fertilized embryos, the efficiency of blastocyst production can be greatly increased compared to when a culture dish made of plastic which has been used in the prior art.

Next, in order to confirm the bottom structure of a PDMS-based culture dish efficient for in vitro culture of embryos, in vitro fertilized embryos were cultured in each of a PDMS-based culture dish having a flat bottom structure (flat bottom) and a PDMS-based culture dish having a cylinder-shaped hole (cylinder-shaped hole) at 37° C. in a 5% $CO_2$ atmosphere for 5 days.

As shown in Table 4 below, the in vitro fertilized embryos cultured in the PDMS-based culture dishes having each of the flat bottom and the cylinder-shaped hole showed no significant difference in the rates of development to the 2-cell and 4-cell stages, but the rates of development of the in vivo fertilized embryos to the blastocyst stage was significantly higher in the PDMS-based culture dish having the cylinder-shaped hole than in the PDMS-based culture dish having the flat bottom.

TABLE 4

Effects of bottom structure of PDMS-based culture plates used for in-vitro culture on preimplantation development of 1-cell ICR mouse embryos generated through in-vitro fertilization.

| Bottom structure of PDMS-based culture plates | No. of embryos[b] cultured | No. (%)[c] of embryos developed to | | |
|---|---|---|---|---|
| | | 2-cell [42][d] | 4-cell [66][d] | Blastocyst [138][d] |
| Flat | 56 | 51 (91.1) | 45 (80.4) | 34 (60.7)[e] |
| Cylinder-shaped hole[a] | 57 | 52 (91.2) | 47 (82.3) | 44 (77.2)[f] |

Model effects of treatments in each parameter, as indicated by p values, were 0.9769, 0.6453 and 0.0377 in the development to the 2-cell, 4-cell and blastocyst stages, respectively.
[a]Bottom has a cylinder-shaped hole with 3.5 mm diameter and 4 mm height and one-cell embryos were cultured in this chamber.
[b]One-cell embryos with pronucleus and second polar body were collected at 6 hours after incubating mature oocytes retrieved by oviduct flushing 16 hours post-hCG injection with spermatozoa.
[c]Percentage relative to the number of embryos cultured.
[d]Numbers in parentheses indicate hours post-hCG injection.
Embryos were cultured in BSA-free M16 medium from the onset of culture and BSA (3 mg/ml) was added to M16 medium from 72 hours post-hCG injection.
[e,f]Different subscripts within the same column are significantly different ($p < 0.05$).

These results demonstrate that the use of the PDMS-based culture dish having the bottom structure including the cylinder-shaped hole can greatly increase the efficiency of production of blastocysts from in vitro fertilized embryos. In addition, it is expected that the PDMS-based culture dish having the cylinder-shaped hole structure can be of great help in the mass production of blastocysts from in vitro fertilized embryos.

During a process in which embryos form blastocysts in vivo, the embryos experience various physical stimuli in the oviduct, and artificially mimicking these physical stimuli can be of great help in increasing the in vitro blastocyst formation rate of embryos. Therefore, in the present invention, it was attempted to maximize the efficiency of in vitro blastocyst formation by improving the physical environment of culture dishes or the like which are used in in vitro culture of embryos.

Specifically, in the present invention, polydimethylsiloxane (PDMS), a kind of silicone, was used as a material for making the vessel for in vitro culture of embryos. When in vitro culture of embryos was performed using the in vitro embryo culture vessel made of this material, this culture vessel showed a significantly increased efficiency of blastocyst formation compared to plastic-based in vitro culture vessels which have been previously used.

Thus, the present invention will be of great help in solving problems associated with low blastocyst formation rates in various industries that use embryos.

The above description of the present invention is exemplary, and those of ordinary skill in the art will appreciate that the present invention can be easily modified into other specific forms without departing from the technical spirit or essential characteristics of the present invention.

Therefore, it should be understood that the exemplary embodiments described above are exemplary in all aspects and are not restrictive. For example, each component described to be of a single type can be implemented in a distributed manner. Likewise, components described to be distributed can be implemented in a combined manner.

The scope of the present invention is defined by the following claims rather than by the detailed description of the invention. It shall be understood that all modifications and embodiments conceived from the meaning and scope of the claims and their equivalents are included in the scope of the inventive concept.

What is claimed is:

1. A device for in vitro culture of embryos, consisting of:
an array having at least one well formed therein; and
a bottom surface formed in the at least one well, wherein:
  the well has a cylindrical shape;
  a diameter at a top of the well is equal to a diameter at a bottom of the well,
  a side surface of the well is vertical to the bottom surface of the well;
  a width and a height of the well, respectively, range from 5 mm to 20 mm; and
  a single groove is formed in the bottom surface of the well, a side surface of the single groove being vertical to a bottom surface of the single groove, the single groove having the width ranging from 2 mm to 5 mm and the height ranging from 2 mm to 5 mm, wherein the bottom surface of the single groove is entirely closed to receive the embryos as an embryo-receiving part, and the single groove is non-removable after receiving the embryos,
wherein the side surface of the well, the bottom surface of the well, the side surface of the single grove, and the bottom surface of the single groove are made of a same material which is a mixture of polydimethylsiloxane (PDMS) and a curing agent at a weight ratio ranging 50:1 to 2:1.

2. The device of claim 1, wherein the well is formed in plural numbers in a solid body in an arrayed fashion.

3. The device of claim 1, which is a device for culturing the embryos in vitro to a blastocyst stage.

4. The device of claim 1, wherein the bottom surface is formed by curing of the polydimethylsiloxane (PDMS).

5. The device of claim 1, wherein the bottom surface is formed by removing bubbles from liquid polydimethylsiloxane (PDMS) injected into the well, followed by curing.

6. A method for in vitro culture of embryos, comprising the steps of:
  injecting the embryos into a well of the in vitro culture device as set forth in claim 1; and
  culturing the embryos.

7. The method of claim 6, wherein culturing the embryos comprises culturing the enbryos to a blastocyst stage.

* * * * *